(12) United States Patent
Bhandari et al.

(10) Patent No.: US 8,889,829 B2
(45) Date of Patent: Nov. 18, 2014

(54) METHODS OF MAKING A DIAGNOSTIC COMPOSITION AND COMPOSITIONS THEREFROM

(75) Inventors: Paridhi Bhandari, Bangalore (IN); Dhananjaya Dendukuri, Bangalore (IN); Vijayakumar Ganapathy, Kanchipuram (IN); Srinivasan Kandaswamy, Little Kanchipuram (IN); Diya Lewis, Chennai (IN)

(73) Assignee: Achira Labs Pvt. Ltd., Bangalore (IN)

( * ) Notice: Subject to any disclaimer, the term of this patent is extended or adjusted under 35 U.S.C. 154(b) by 0 days.

(21) Appl. No.: 13/702,994

(22) PCT Filed: Sep. 3, 2010

(86) PCT No.: PCT/IB2010/053974
§ 371 (c)(1),
(2), (4) Date: Jan. 17, 2013

(87) PCT Pub. No.: WO2012/004635
PCT Pub. Date: Jan. 12, 2012

(65) Prior Publication Data
US 2013/0109837 A1 May 2, 2013

(30) Foreign Application Priority Data
Jul. 5, 2010 (IN) ............................ 1909/CHE/2010

(51) Int. Cl.
*A61K 38/17* (2006.01)
*C07K 17/02* (2006.01)
*D01C 3/02* (2006.01)
*G01N 33/544* (2006.01)
*C07K 14/435* (2006.01)

(52) U.S. Cl.
CPC . *C07K 17/02* (2013.01); *D01C 3/02* (2013.01); *G01N 33/544* (2013.01); *C07K 14/435* (2013.01); *G01N 2333/43578* (2013.01)
USPC ........................................................ 530/353

(58) Field of Classification Search
None
See application file for complete search history.

(56) References Cited

U.S. PATENT DOCUMENTS

2003/0100108 A1\* 5/2003 Altman et al. ................. 435/395
2004/0224406 A1\* 11/2004 Altman et al. ................. 435/395

FOREIGN PATENT DOCUMENTS

WO    WO 2012/004635    1/2012

OTHER PUBLICATIONS

Lu et al., "Degradation Mechanism and Control of Silk Fibroin", Biomacromolecules. Apr. 11, 2011; 12(4): 1080-1086. doi:10.1021/bm101422j.\*

Lee et al., "Immobilization fo Trypsin onto Silk Fibroin Fiber via Spacer Arms", International Journal of Industrial Entomology, 2004, 8(2): 195-200.\*
Altman et al., "Silk-based biomaterials," *Biomaterials*, 24 (3), pp. 401-416, 2003.
Becker et al., "Polymer microfluidic devices," *Talanta*, 56 (2), pp. 267-287, Feb. 11, 2002.
Davarpanah S. et al., "Environmentally friendly surface modification of silk fiber: Chitosan grafting and dyeing" *Applied Surface Science*, 255 (7), pp. 4171-4176, Jan. 15, 2009.
Klank, H. et al., "CO(2)-laser micromachining and back-end processing for rapid production of PMMA-based microfluidic systems," *Lab on a Chip*, 2 (4), pp. 242-246, Dec. 2002.
Li, X. et al., "Thread as a Versatile Material for Low-Cost Microfluidic Diagnostics," *ACS Applied Materials & Interfaces*, 2 (1), pp. 1-6, Dec. 9, 2009.
Martinez et al., "Patterned paper as a platform for inexpensive, low-volume, portable bioassays," *Angew Chem Int Ed Engl*, 46 (8), pp. 1318-1320, 2007.
McDonald et al., "Poly(dimethylsiloxane) as a material for fabricating microfluidic devices," *Acc Chem Res*, 35 (7), pp. 491-499, Jul. 2002.
McFarland et al., "Color My Nanoworld," *J. Chem. Educ.*, 81(4), 544A, Apr. 2004.
Oliver, C. "Conjugation of Colloidal Gold to Proteins," *Methods in Molecular Biology*, vol. 115, pp. 331-334, Jan. 15, 1999: Immunocytochemical Methods and Protocols, Edited by: L. C. Javois © Humana Press Inc., Totowa, NJ.
Pu, Q. et al., "On-chip micropatterning of plastic (cylic olefin copolymer, COC) microfluidic channels for the fabrication of biomolecule microarrays using photografting methods," *Langmuir*, 23 (3), pp. 1577-1583, Jan. 30, 2007.
Vepari et al., "Silk as a biomaterial," *Progress in Polymer Science*, 32 (8-9), pp. 991-1007, Aug. 7, 2007.
Yager et al., "Point-of-care diagnostics for global health," *Annu Rev Biomed Eng*. 10, pp. 107-144, 2008.

\* cited by examiner

*Primary Examiner* — Suzanne M Noakes
(74) *Attorney, Agent, or Firm* — Levine Bagade Han LLP

(57) ABSTRACT

In one aspect, the invention provides a method for making a hydrophilic-silk composition. The method includes providing at least one strand of silk fiber, treating the silk fiber with an alkaline solution to provide at least one strand of degummed silk fiber, and treating the degummed silk fiber with a treatment solution to provide a hydrophilic-silk composition. The degummed silk fiber or the hydrophilic-silk composition is further immobilized with at least one reagent to make a silk-based diagnostic composition. The invention provides a silk-based diagnostic composition made by the method of the invention, and a diagnostic device that comprises the silk-based diagnostic composition. In another aspect, the invention provides a method of making a diagnostic device. The method includes providing at least one strand of a diagnostic-fiber composition, providing at least one strand of a hydrophobic-fiber composition, inter-weaving the at least one strand of the diagnostic-fiber composition and the at least one strand of the hydrophobic-fiber composition. In one embodiment, the diagnostic-fiber composition and the hydrophobic-fiber composition are both based on silk.

12 Claims, 1 Drawing Sheet

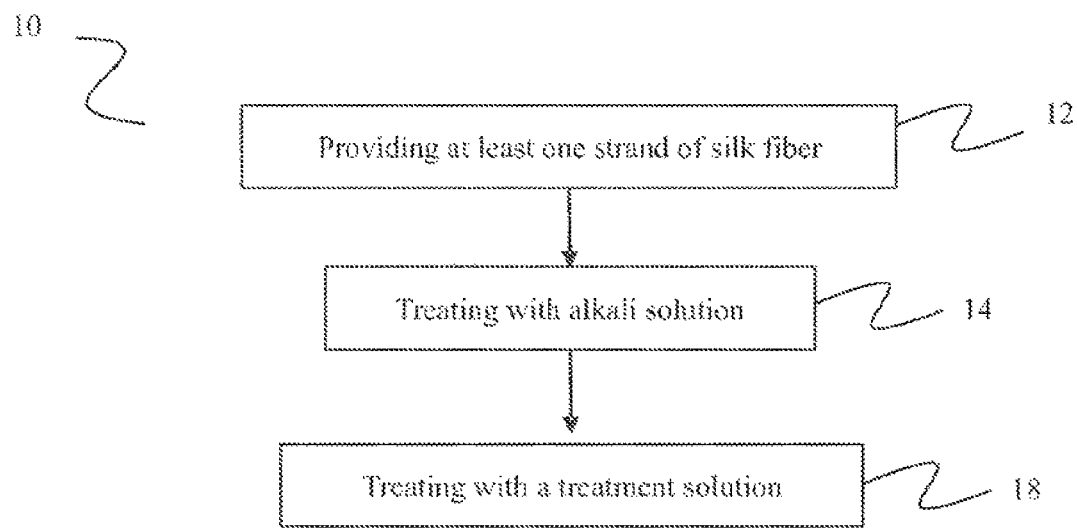

METHODS OF MAKING A DIAGNOSTIC COMPOSITION AND COMPOSITIONS THEREFROM

CROSS-REFERENCE TO RELATED APPLICATIONS

This application is a U.S. National Phase under 35 U.S.C. 371 to PCT International Patent Application No. PCT/IB2010/053974 filed on Jul. 5, 2010, the content of which is incorporated herein by reference in its entirety.

TECHNICAL FIELD

The invention relates generally to methods of making diagnostic composition and more specifically to methods of making silk-based diagnostic composition.

BACKGROUND

The detection of analytes including proteins, DNA/RNA and metabolites from body fluids and other samples of biological origin is essential for a variety of applications including medical testing, toxin detection and forensic analysis. Improved, point-of-care testing of such analytes is an urgent worldwide requirement (Yager, P.; Domingo, G. J.; Gerdes, J., Point-of-care diagnostics for global health. *Annu Rev Biomed Eng* 2008, 10, 107-44). The current systems designed for such applications suffer from several drawbacks such as high costs, bulkiness and delayed results. There is therefore a large unmet need for the development of systems that are low-cost, portable, convenient to handle and show high efficiency towards detection. These systems should also be capable of rapidly identifying a broad range of analytes from samples of biological origin.

Microfluidic, lab-on-a-chip methods have gained prominence over the past decade as solutions to some of these problems. However, existing technologies for the manufacture of microfluidic lab-on-a-chip devices are handicapped by the absence of mature manufacturing processes that can enable the transition of ideas from academic labs to industry. Adaptation of traditional methods used for microelectronic fabrication for this purpose meant that early microfluidic devices were synthesized in glass or silicon. However, these are materials that require expensive processing conditions and high capital investment.

To address this problem, a number of different materials and processing methods have been explored for the fabrication of microfluidic devices (Becker, H.; Locascio, L. E., Polymer microfluidic devices. *Talanta* 2002, 56 (2), 267-287). These materials include plastics such as PDMS (polydimethylsiloxane) (McDonald, J. C.; Whitesides, G. M., Poly(dimethylsiloxane) as a material for fabricating microfluidic devices. *Acc Chem Res* 2002, 35 (7), 491-9), PMMA (polymethylmethacrylate) (Klank, H.; Kutter, J. P.; Geschke, O., CO(2)-laser micromachining and back-end processing for rapid production of PMMA-based microfluidic systems. *Lab Chip* 2002, 2 (4), 242-6) and COC (cyclicolefin copolymer) (Pu, Q.; Oyesanya, O.; Thompson, B.; Liu, S.; Alvarez, J. C., On-chip micropatterning of plastic (cylic olefin copolymer, COC) microfluidic channels for the fabrication of biomolecule microarrays using photografting methods. *Langmuir* 2007, 23 (3), 1577-83). Plastics are relatively cheap and they have advantages such as their processability, transparency and the ability to form intricate patterns down to the micron scale. However, they also suffer from some disadvantages such as their natural hydrophobic nature which precludes simple capillary flow, their carbon footprint and the lack of mature manufacturing methods that are easily adaptable for large scale microfluidic plastic chip fabrication. Further, for the plastic-based microfluidic devices, sophisticated and expensive readers that can direct fluid flow and can provide a read-out from the plastic chip are still required, which renders the entire device and operation unsuitable for very low-cost and robust point-of-care diagnostics.

On the other hand, paper-based lateral flow immunoassays (LFIs) have been hugely successful in the market place with a variety of rapid tests such as home pregnancy tests being widely available. Visual readouts in the form of a color change are used for detection while sample flow occurs automatically through capillary action. Further, mature manufacturing processes are already available for such devices. However, LFIs come with a set of disadvantages too. They are not very reliable and do not provide for the ability to perform multiplex tests. One of the reasons for this is the lack of an ability to define a 'flow-path' in a paper based device (Martinez, A. W.; Phillips, S. T.; Butte, M. J.; Whitesides, G. M., Patterned paper as a platform for inexpensive, low-volume, portable bioassays. *Angew Chem Int Ed Engl* 2007, 46 (8), 1318-20).

Recently, the Whitesides group advanced such technology by patterning paper into selectively hydrophilic and hydrophobic portions. A patterned flow field can therefore be defined. However, paper-based devices still have some problems like the lack of mechanical stability and the absence of low-cost manufacturing methods that can deposit multiple reagents without heat treatment or exposure to high stress. Very recently, cotton thread has also been explored as a medium for microfluidic chip fabrication (Li, X.; Tian, J.; Shen, W., Thread as a Versatile Material for Low-Cost Microfluidic Diagnostics. *ACS Applied Materials & Interfaces* 2009, 2 (1), 1-6). Experiments were performed on single cotton threads or cotton threads that have been sewed onto a plastic substrate and color change based readouts were used to detect the presence of a reagent. These experiments are not necessarily conducive towards development of high-throughput and reproducible methods for manufacture of point-of-care diagnostic devices using either the cotton fibers or other suitable materials. Hence, there remains a dire need in the art that addresses all the problems associated with diagnostic devices, their manufacture, cost and reliability.

BRIEF DESCRIPTION

In one aspect, the invention provides a method for making a hydrophilic silk composition. The method comprises providing at least one strand of silk fiber. The method then involves treating the at least one strand with an alkaline solution to provide at least one strand of degummed silk fiber. Subsequently, the at least one strand of degummed silk fiber is treated with a treatment solution. The invention also provides a method for providing a silk-based composition. The method comprises immobilizing at least one reagent onto the at least one strand of degummed silk or to the hydrophilic silk fiber to provide at least one strand of the silk-based diagnostic composition.

In another aspect the invention provides a silk-based diagnostic composition, wherein the silk-based diagnostic composition is made by the method of the invention.

In yet another aspect, the invention provides a diagnostic device that comprises the silk-based diagnostic composition of the invention.

DRAWINGS

These and other features, aspects, and advantages of the present invention will become better understood when the following detailed description is read with reference to the accompanying drawings in which like characters represent like parts throughout the drawings, wherein:

FIG. 1 is a flowchart representation of the exemplary steps of the method for making a hydrophilic silk composition of the invention.

DETAILED DESCRIPTION

As used herein and in the claims, the singular forms "a," "an," and "the" include the plural reference unless the context clearly indicates otherwise.

Strand as used herein refers to a single element (as a yarn or thread) of a woven or plaited material.

Analyte, as used herein, refers to a substance or chemical constituent that is determined in an analytical procedure. For instance, in an immunoassay, the analyte may be a protein ligand or a binder, while in blood glucose testing, the analyte is glucose. In one instance, the analyte could be a gene that is a marker for the Hepatitis-B virus. In another exemplary instance, analyte may include a drug to be detected, such as cocaine from a blood analysis. The analytical procedure may include, for instance, fluorescence, mass-spectrometry, colorimetry, radio-imaging, electrochemical detection and the like, and combinations thereof. In some instances, analytes may refer to antibodies. In other instances, analytes may refer to antigens.

Antibody as used herein refers to protein that is used in the identification of specific antigen. The specific antigen is typically a marker of a disease or certain types of diseases. Sometimes, antibodies may also be referred to as immunoglobulins. Antibody may be primary or secondary antibody. Primary antibodies are antibodies raised against a specific antigen and are generally unlabelled. Primary antibodies may also be referred to as capture antibodies. Secondary antibody is an antibody that binds to primary antibody or fragments contained within the primary or capture antibody. Secondary antibody comprise label that render them useful for detection. Typical labels include fluorescence moiety, radio-active compounds, enzyme-linked labels, magnetically active particles, nanoparticles, quantum dots, latex particle labels, and the like, and combinations thereof. Depending on the label, the method used to detect, identify and quantitate may include fluorescence spectroscopy, radio-imaging, ELISA test and the like.

Antigen, as used herein, refers to a molecule that is recognized by an immune system of a living organism. Antigen also refers to molecular fragments that may be recognized by the immune system. It is generally known that a given antigen shows specificity to an antibody, and this property of an antigen is used in a variety of applications.

As stated herein, in one aspect the invention provides a method for making a hydrophilic-silk composition. The exemplary steps in the method of the invention, represented by numeral 10, are shown in a flowchart representation in FIG. 1. The silk-based diagnostic composition of the invention is a derivative of silk. Silk is a fiber obtained from silkworms, more specifically from the larvae of mulberry silkworms. The silk most useful in the invention are those that can be woven into textiles, such as that obtained from the silkworm *Bombyx Mori*, however, other forms of silk that may be synthetically made or produced from other sources may also be used for this invention. Chemically, silk fiber comprises a chain of amino acids, which possesses functional groups that may be further used for binding useful moieties. As used herein, functional groups are reactive chemical moieties that can interact with other reactive species to form physical or chemical bonds.

The method of the invention includes providing at least one strand of a silk-fiber, which is represented by numeral 12 in FIG. 1. This may typically involve isolating at least one strand of a silk fiber obtained from a suitable silkworm. The silk fiber is then treated with an alkali solution to form at least one strand of degummed silk, represented by numeral 14 in FIG. 1. The alkali solution useful in the invention is typically obtained by the dissolution of a compound having a strong basicity in an aqueous mixture. Typical compounds having strong basicity include, but not limited to, sodium hydroxide, potassium hydroxide, lithium hydroxide, calcium hydroxide, ammonium hydroxide and the like, and mixtures thereof. Treatment methods may include immersing the silk fiber into an alkali solution, spraying the silk-fiber with the alkali solution, or any such variation known to those skilled in the art. Without being bound to any theory or principle, it is known to one skilled in the art that silk fibers obtained in its natural state comprises a coating of a gummy mixture comprising a protein named sericin and that the alkaline solution can be used to efficiently remove the coating (Altman, G. H.; Diaz, F.; Jakuba, C.; Calabro, T.; Horan, R. L.; Chen, J.; Lu, H.; Richmond, J.; Kaplan, D. L., Silk-based biomaterials. *Biomaterials* 2003, 24 (3), 401-416). An optional washing step may be included to wash off the excess alkali or other extraneous material.

The degummed silk fiber is then treated with a treatment solution in the method of the invention to form the hydrophilic-silk composition, represented by numeral 18 in FIG. 1. The treatment solution typically comprises an aqueous-based solvent. Aqueous-based solvent may include, for example, aqueous-based buffers, deionized water, water comprising ethylene glycol, and the like. The treatment solution comprises a blocking agent. Blocking agents are used to protect functional groups on the degummed silk fiber so they don't interfere with the subsequent steps, such as antibody immobilization, detection etc. Blocking agents may be any chemical compound that possesses a complementary functional group to the functional group available on the degummed silk fiber or comprise groups that enable the agent to bind to the silk fiber through non-specific interactions such as hydrophobic interactions. Complementary functional groups towards a functional group are those that can react with the functional group through a physical or chemical bond. For example, for a functional group carboxylic acid, a complementary functional may be an amine, which can form a salt or react to form an amide bond. Similarly, a hydroxyl group can react with a carboxylic acid to form an ester. In one embodiment of the invention, the blocking agent is a bovine serum albumin, generally abbreviated as BSA. In another embodiment, the blocking agent is a milk powder.

The treatment solution further comprises a surfactant. Without being bound to any theory, the surfactant treated degummed silk fiber is expected to facilitate the flow of aqueous-based fluids on surface of the fiber. Typical surfactants useful in the invention include, but not limited to, ionic surfactants such as perfluorooctanoate, perfluorooctanesulfonate, sodium dodecyl sulfate, ammonium lauryl sulfate, and other alkyl sulfate salts, sodium laureth sulfate, alkyl benzene sulfonate, cetyl trimethylammonium bromide, cetylpyridinium chloride, polyethoxylated tallow amine, benzalkonium chloride, benzethonium chloride, (3-[(3-cholamidopropyl)dimethylammonio]-1-propanesulfonate), dodecyl betaine, cocamidopropyl betaine, cocoampho glycinate; nonionic surfactants such as alkyl poly(ethylene oxide), poly(vinyl alcohol), sorbitan derivatives based on poly(ethylene glycol), including the Tween® series (ex. Tween® 20, Tween® 80), Span® series (ex. Span® 80) the Brij® series (ex. Brij® 72), the Triton® series (ex. Triton X-100), alkylphenol poly(ethylene oxide), copolymers of poly(ethylene oxide) and poly(propylene oxide) including the Pluronic® series (ex. Pluronic® F-127), alkyl polyglucosides, including: octyl glucoside, decyl maltoside, fatty alcohols such as cetyl alcohol, oleyl alcohol, dodecyl dimethylamine oxide; and the like. In one exemplary embodiment, the surfactant is a polysorbate based on poly(ethylene glycol), also sometimes referred to as sorbitan derivatives. In one specific exemplary embodiment, the surfactant is a Tween® 20.

The treatment solution may further comprise a poly(ethylene glycol). Poly(ethylene glycol), as one skilled in the art will appreciate, is available in a wide variety of molecular sizes, chain lengths, degree of branching and branch lengths, crosslinking, and other molecular variations. Any of the poly (ethylene glycol) with the appropriate molecular characteristics may be useful in the invention. Poly(ethylene glycol) having a particular molecular weight and linearity is commercially available from several sources. The hydrophilic polymer facilitates control of viscosity of fluids flowing on the surface of the silk-based diagnostic composition. One skilled in the art will be able to recognize that the rate of flow of fluids on the surface of the silk-based diagnostic composition may be controlled in a facile manner through the appropriate choice of the components and the concentration of the various components of the treatment solution without undue experimentation.

An optional washing step may be included to remove any extraneous material, excess material and/or unbound material from the hydrophilic-silk composition.

The method of the invention may further comprise a step of immobilizing at least one reagent onto the at least one strand of the hydrophilic-silk composition to form at least one strand of silk-based diagnostic composition, not shown in FIG. 1. Alternately, the method of the invention may comprise a step of immobilizing at least one reagent onto the at least one strand of degummed silk fiber, followed by treatment with a treatment solution to form the at least one strand of silk-based diagnostic composition, also not shown in FIG. 1. As already noted, silk fiber comprises functional groups. The reagent may be immobilized onto the degummed silk or the hydrophilic-silk composition by suitably exploiting the functional groups. The immobilization may be achieved through a wide variety of techniques known to those of ordinary skill in the art. The techniques may include, such as, but not limited to, immersing, covalent bonding, coating, dipping, stamping, or combinations thereof. Using one or more of the aforementioned techniques, simple physical attachment or chemical bonding of the reagent to the silk may be achieved. An optional washing step may be included to remove any excess unbound reagent and other extraneous material. Thus, a silk-based diagnostic composition may be obtained.

Analytes that may be detected using the invention may include any chemical such as narcotic or explosives, antibodies, antigens, nucleic acids and the like. Antibodies, when present as the first reagents, are typically primary antibodies. Antibodies that may be used for immobilization may include, such as, but not limited to, Anti-hcG, Anti-HIV-p24, Anti-HIV-gp120, Anti-FSH, Anti-TSH, Anti Troponin, and Anti *Plasmodium Falciparum*, and the like.

Antigens useful as the first reagent in the invention include, for example, p24, gp120, gp41, HIVII—gp105, gp36, Hepatitis C—NS3, NS5, core antigen, β-Hcg (pregnancy), TSH (thyroid), FSH (female hormone), Troponin-T (cardiac), CpkMb, BNP, Myoglobin, Hb1Ac, PSA, AFP, CEA, CA125, CA19.9, Progestorone, Testosterone, Estradiol. As stated herein, the method of the invention includes immobilizing at least one reagent. When the method includes immobilizing a second reagent, the second reagent may be a secondary antibody. In some embodiments, the second reagent is a secondary antibody. When the second reagent is a secondary antibody, then the silk-based diagnostic composition is formed in such a way that the secondary antibody is present upstream from the primary antibody. Forming the composition in this manner ensures that when a fluid is allowed to flow along the composition, the secondary antibody is exposed to the fluid before the primary antibody. Such compositions are very useful for sandwich-type immunoassays, wherein the secondary antibody comprises a detectable group and forms a sandwich-like structure with the primary antibody and the antigen.

A typical manifestation of the silk-based diagnostic composition of the invention is in the form of woven fibers. However, other forms of the silk-based diagnostic composition may also be contemplated. This may include, for example, a film structure, a single strand, a cylinder, and the like. The exact nature of the silk-based diagnostic composition to be used in the final application will be obvious to one skilled in the art.

In one embodiment, the silk-based diagnostic composition is used as a fibrous material that is woven together. An important criterion to pick a fibrous material suitable for making the silk-based diagnostic composition is its mechanical stability and the existence of manufacturing methods that are both precise enough to make intricate patterns and scalable such that large numbers of silk-based diagnostic compositions can be produced at a low cost. Silk is a material that fits both these criteria, and further, possesses other desirable properties such as being a natural fiber, biodegradable. Being a polypeptide, silk offers a number of functional groups that can be used to functionalize biomolecules. Further, silk weaving offers the ability to introduce particular functionalities into a pattern without resorting to high temperature or high shear processing. This involves simply treating the thread and incorporating it into a particular spot using weaving.

The method of the invention is particularly attractive as it is conducive for scale-up for manufacturing a large number of diagnostic devices within a given period of time. The method of the invention further uses skill and equipment that already exist. In this invention, the adaptability of the existing methods in the textile manufacturing for the production of diagnostic device manufacture has been demonstrated successfully. The adaptation involves careful choice of materials and their preparation, and slight modification of the techniques to suit the requirements. Economic feasibility of the materials and methods also make this a viable option.

The silk-based diagnostic composition comprises two ends, of which one of them is designated as a sample introduction port. Typically, sample for analysis is introduced into the diagnostic-fiber composition as an aqueous solution or an aqueous suspension or an aqueous emulsion. It will be understood by one skilled in the art that the sample may be introduced at any point on the silk-based diagnostic composition. The sample may comprise an analyte to be analyzed. The nature of the analysis may be manifold. For example, in one embodiment, the analysis may involve determining presence or absence of an analyte. In another embodiment, the analysis may involve the concentration and/or amount of an analyte present in a sample. In some other embodiments, a combination thereof, which may include determining the presence or absence of an analyte, and if present, the amount and/or concentration of the analyte in the sample is to be determined. After introduction of the sample in the sample introduction port, the sample flows along the diagnostic-fiber composition. Without being bound to any theory, the flow of solution through the diagnostic-fiber composition is governed by capillary action, also sometimes referred to as wicking action in the art. Typical samples include, but not limited to, sweat, blood, urine, semen, and the like. Sample, as used herein, includes the entire fluid, or it may mean a component of the fluid that is being analyzed for. The flow path culminates at an another end of the silk-based diagnostic composition that may be designated as an absorption port. In one embodiment, the reagent is present at a certain position on the diagnostic-fiber composition, and the absorption port is present in a flow direction that is past the position of the reagent on the diagnostic fiber composition such that the sample flows past the reagent and ends at the absorption port. In another embodiment, the reagent is added in a suitable manner known in the art, such that the reagent immobilization is achieved in situ. Subsequently, the sample is introduced onto the diagnostic-fiber composition. When the sample comprising the analyte and the reagent interact, they become bound and form a complex, and the complex stops flowing, while the solution flows till it reaches the absorption port. In case, the sample does not comprise the analyte, no complex is formed, and hence, the flow continues till it reaches the absorption port.

In situations wherein a secondary reagent is present, the sample comes in contact with the secondary reagent first as it is present upstream from the primary reagent and the analyte, if present, forms a first complex with the secondary reagent, following which the flow of the solution comprising the first complex reaches the primary reagent forming a second complex comprising the analyte, primary reagent and secondary reagent. The second complex stops flowing at this point. If the sample does not comprise the analyte, then the first complex and the second complex does not form, and the sample flows until it reaches the absorption port. The solution stops flow when there are no more flow regions remaining on the silk-based diagnostic composition. Further steps to remove unbound secondary reagent by washing it past the primary reagent by the excess sample fluid may also be contemplated. The analysis of the complex may be achieved through methods already known to those skilled in the art. Such methods may include, for example, fluorescence, confocal microscopy, optical microscopy, colorimetry, electrochemical methods, and the like, and combinations thereof.

In some embodiments, the sample port may comprise a material that may facilitate addition of the sample and may further be useful in other additional functions, such as separating components. Some exemplary functions useful herein include separation of blood cells from fluids, separation of higher molecular weight components from low molecular materials, and the like. Specific compositions for achieving are known in the art, and may be suitably employed herein.

In some other embodiments, the absorption port may further comprise an absorbent material, such as cotton, nitrocellulose, poly(acrylic acid), and the like to facilitate flow of sample.

A typical silk-based diagnostic composition may also comprise a marking to indicate the point to indicate the sample introduction port to a user. The amount of sample necessary to obtain a useful analysis from the silk-based diagnostic composition of the invention will depend on the configuration of the silk-based diagnostic composition and may be arrived at without undue experimentation by one skilled in the art.

The silk-based diagnostic composition of the invention may further comprise colorants, emollients, other additives for various purposes, along with those mentioned herein. These additives may be for cosmetic purposes, to provide extra features, or add greater functionality to the existing diagnostic device. Further, the silk-based diagnostic composition of the invention may be mounted onto a substrate. The substrate may be present to provide strength and mechanical integrity to the silk-based diagnostic composition. The substrate may be chosen from any number of strong materials known to those skilled in the art, and may include, for example, metal backing such as steel, iron, titanium, alloys, and the like, plastics such as poly(methyl methacrylate), polystyrene, polyethylene, polypropylene, and the like, cardboard, wood, and others, and combinations thereof.

The silk-based diagnostic composition of the invention may further be contemplated to be encased in a suitable enclosure to protect it from environmental factors, such as handling during transportation, sunlight, moisture, humidity, and so on. In such instances, the enclosure may be designed in such a way that it can be opened to allow access to the device. Alternately, the enclosure may be present in such a way that there is an opening only for the sample introduction port, so that the rest of the device is totally enclosed even during operation. Enclosures suitable for the device may have properties such as transparency, strength, water resistance, moldability, and the like. Some useful materials that can perform well as enclosures for the device may include, but not limited to, glass, plastics such as poly(methyl methacrylate), polystyrene, polyethylene, polypropylene, and the like.

The invention as described herein provides weaving as an alternate manufacturing technology for the manufacture of silk-based diagnostic composition, and further fabric-based diagnostic devices that may also be referred to as 'fab chips'. Such diagnostic devices may be reusable type or may be a single-use, disposable device. Silk weaving is an art that has developed to a very high degree of skill in many parts of the world, and intricate patterns whose dimensions are limited only to the thickness of an individual thread may be woven in a highly parallelized manner. This technique is capable of being adapted for use in the instant invention.

The silk-based diagnostic composition of the invention may be used for any assays to be performed in a wide variety of applications. For example, in case of using the silk-based diagnostic composition of the invention for a sandwich immunoassay, sample for qualitative detection of antigen in the sample is introduced on to the sample port of silk-based diagnostic composition. After introduction, as the sample flows along the silk-based diagnostic composition due to capillary action, it comes in contact with secondary reagent (detection antibody) first, as it is present upstream from the primary reagent (capture antibody). Analyte (antigen) if present, forms a first complex with secondary reagent. Following this, the flow of the solution comprising the first complex reaches the primary reagent (capture antibody) forming a second complex comprising the analyte, primary reagent and secondary reagent. The second complex stops flowing at this point and can be visualized as pink/red color band. If the sample does not comprise the analyte, then the first complex and the second complex does not form, and the sample flows until it reaches the absorption port. The solution stops flow when there are no more flow regions remaining on the device.

In the case of the use of the silk-based diagnostic composition of the invention for an indirect immunoassay, the sample for the qualitative detection of antibody is introduced on to the sample port. After introduction, as the sample flows along the silk-based diagnostic composition due to capillary action, it comes in contact with secondary reagent (detection antibody) first, as it is present upstream from the primary reagent (capture antigen). Analyte (antibody) if present, forms a first complex with secondary reagent. Following this, the flow of the solution comprising the first complex reaches the primary reagent (capture antigen) forming a second complex comprising the analyte, primary reagent and secondary reagent. The second complex stops flowing at this point and can be visualized as pink/red color band. If the sample does not comprise the analyte, then the first complex and the second complex does not form, and the sample flows until it reaches the absorption port. The solution stops flow when there are no more flow regions remaining on the device.

EXAMPLE

Hydrophilic Fiber Composition

Natural silk fiber contains a waxy outer covering that must be removed by a process called degumming. Hydrophilic silk threads that permitted capillary flow were made by degumming the natural silk fiber by immersing the silk thread in a solution of 1M NaOH. The thread was then immersed in a solution containing 0.1% Tween® 20, Bovine Serum Albumin (BSA) and 1% PEG (MW 400). This treated thread was found to have more uniform flow properties and also prevented the non-specific binding of protein to the silk thread.

Capture Antibody/Antigen Coating on Threads

Since the degummed silk non-specifically binds to proteins, capture antibody was directly coated onto the hydrophilic fiber composition by immersing the hydrophilic fiber composition in an immunoglobulinG solution containing 1 mg/mL protein in Tris buffered saline.

Secondary Antibody Coating on Threads 40 nm sized Gold-conjugated secondary antibody was prepared using known methods (.A. D. McFarland, C. L. Haynes, C. A. Mirkin, R. P. Van Duyne and H. A. Godwin, "Color My Nanoworld," *J. Chem. Educ.* 2004, 81, 544A; Secondary antibody conjugation to gold—Conjugation of Colloidal Gold to Proteins by Constance Oliver From: Methods in Molecular Biology, Vol. 115: Immunocytochemical Methods and Protocols Edited by: L. C. Javois© Humana Press Inc., Totowa, N.J.) The secondary antibody labeled gold solution, which was a clear, dark pink colored solution, was applied to the silk thread after first treating the silk thread with a solution containing 1% sucrose, 0.2% Tween 20, 1% Bovine Serum Albumin (BSA) and 1% poly(ethylene glycol) (Molecular Weight 400).

Coated Thread Incorporation

The capture antibodies and labeled secondary antibody coated thread was inserted at specified points between the hydrophilic warp threads manually, by a weaver, using individually labeled spools. Specific threads in the Jacquard controlled system are lifted and the coated thread is run through them using the shuttle. This results in coated thread being interwoven at multiple points in the fabric.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. A method for making a silk-based diagnostic composition, said method comprising:
   providing at least one strand of silk fiber;
   treating the at least one strand of silk fiber with an alkaline solution to provide at least one strand of de gummed silk fiber;
   immobilizing at least one reagent onto the at least one strand of degummed silk fiber to provide a reagent-immobilized silk-fiber; and
   treating the reagent-immobilized silk-fiber with a treatment solution comprising poly(ethylene glycol) based sorbitan derivative, Bovine Serum Albumin (BSA) and 1% PEG 400 to provide a silk-based diagnostic composition.

2. A method of making a silk-based diagnostic composition, wherein the method comprises:
   providing at least one strand of silk fiber;
   treating the at least one strand of silk fiber with an alkaline solution to provide at least one strand of de gummed silk fiber;
   treating the at least one strand of de gummed silk fiber with a treatment solution comprising poly(ethylene glycol) based sorbitan derivative, Bovine Serum Albumin (BSA) and 1% PEG 400 to provide a hydrophilic-silk composition; and
   immobilizing at least one reagent onto the hydrophilic-silk composition to provide a silk-based diagnostic composition.

3. The method of claim 1 or 2, wherein the treatment solution comprises an aqueous solution of a surfactant.

4. The method of claim 3, wherein the surfactant is a sorbitan derivative.

5. The method of claim 3, wherein the surfactant further comprises poly(ethylene glycol).

6. The method of claim 1 or 2, wherein the blocking agent is bovine serum albumin.

7. The method of claim 1 or 2, wherein the at least one reagent is a primary antibody.

8. The method of claim 7, wherein the primary antibody is selected from a group consisting of Anti-hcG, Anti-HIV-p24, Anti-HIV-gp120, Anti-FSH, Anti-TSH, Anti Troponin, and Anti *Plasmodium Falciparum*.

9. The method of claim 1 or 2, wherein the at least one reagent is a secondary antibody.

10. The method of claim 9, wherein the secondary antibody is selected from the group consisting of gold or latex conjugated Anti-hcG, Anti-HIV-p24, Anti-HIV-gp120, Anti-FSH, AntiTSH, Anti Troponin, and Anti *Plasmodium Falciparum*.

11. The method of claim 1 or 2, wherein the at least one reagent is an antigen.

12. The method of claim 1 or 2, wherein the immobilizing is achieved by a method selected from the group consisting of immersing, covalent bonding, coating, dipping, stamping, or combinations thereof.

\* \* \* \* \*